United States Patent [19]

Gallagher

[11] 4,173,046
[45] Nov. 6, 1979

[54] ABSORPTIVE PATIENT UNDERPAD

[76] Inventor: John P. Gallagher, 88 Ashley Ave., Charleston, S.C. 29401

[21] Appl. No.: 823,418

[22] Filed: Aug. 10, 1977

[51] Int. Cl.² ........................ E03C 11/10; A61F 13/00
[52] U.S. Cl. ........................................ 5/484; 128/296; 5/487; 5/500
[58] Field of Search ............... 128/296, 287, 153, 152, 128/149, 156; 5/91, 327 R, 335, 334 R, 92; 428/315, 508, 138

[56] References Cited

U.S. PATENT DOCUMENTS

| | | | |
|---|---|---|---|
| 2,896,618 | 7/1959 | Schaefer | 128/156 |
| 3,670,345 | 6/1972 | Doll et al. | 5/91 |
| 3,757,356 | 9/1973 | Freeman | 5/91 |
| 3,927,673 | 12/1975 | Taylor | 128/287 |
| 3,989,867 | 4/1976 | Sisson | 5/91 |
| 4,069,366 | 1/1978 | Hoey | 428/310 |

*Primary Examiner*—Robert W. Michell
*Assistant Examiner*—C. W. Shedd
*Attorney, Agent, or Firm*—Harold L. Stowell

[57] ABSTRACT

An absorptive and protective patient underpad is characterized by its ability to absorb substantial volumes of liquid, while maintaining a relatively dry top surface and the underpad is further characterized by a layer between a top cushioning layer and a lower absorbent layer which will permit liquid flow into the absorbent layer and reduce to a minimum the generation and release of offensive odors from the absorbent layer.

1 Claim, 3 Drawing Figures

U.S. Patent  Nov. 6, 1979  4,173,046
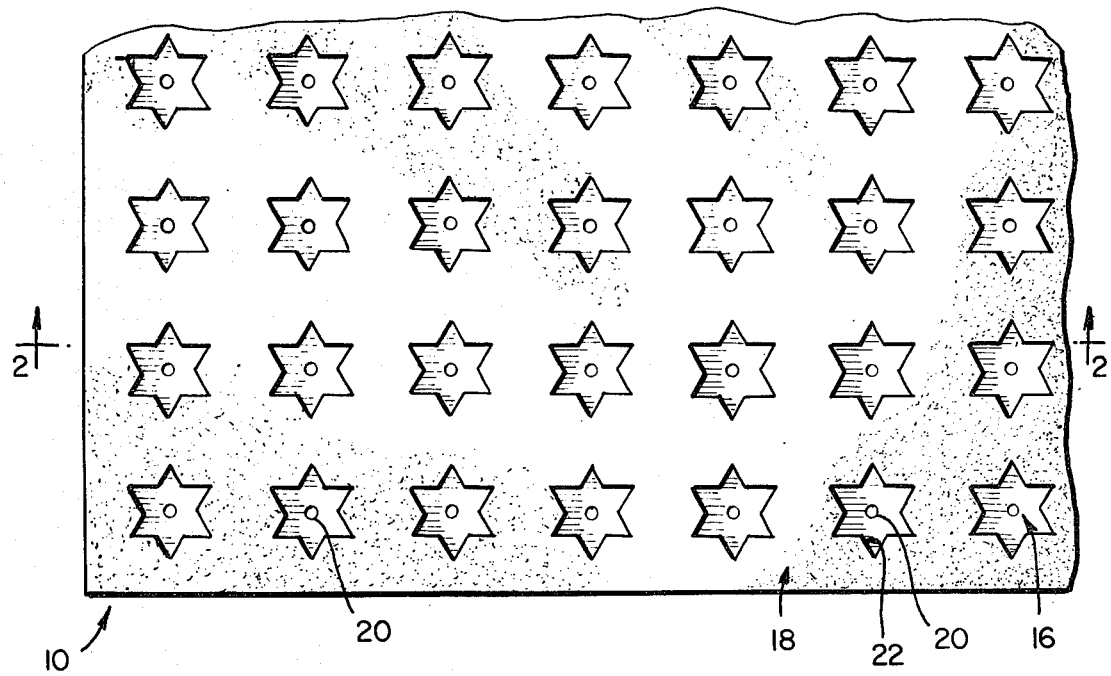
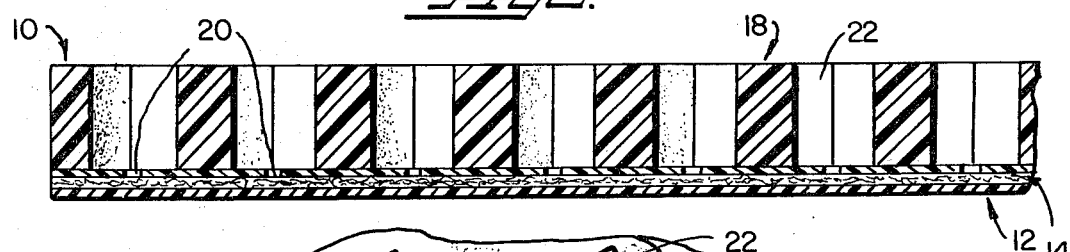
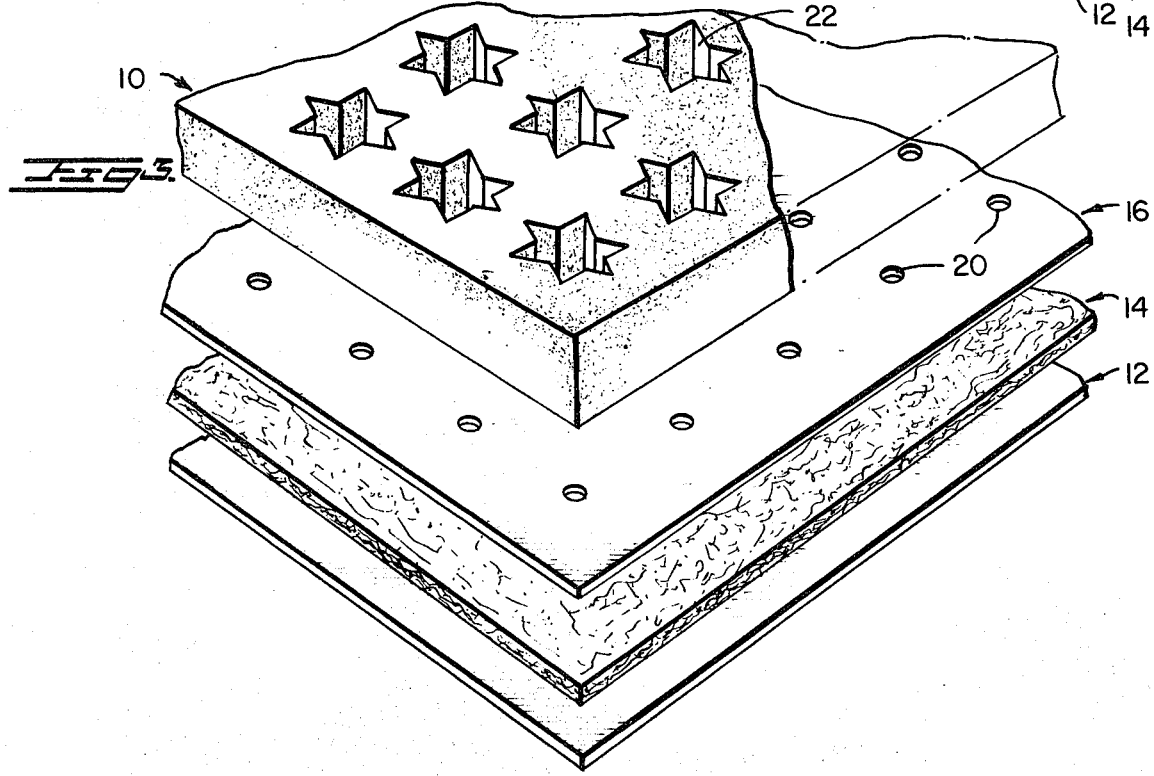

ABSORPTIVE PATIENT UNDERPAD

BACKGROUND OF THE INVENTION

1. Field of the Invention

This invention relates to a bed pad to be used on beds being utilized by invalid patients and the like. In the past in nursing homes, hospitals, private homes and the like where invalid patients are bedridden, problems have arisen due to failure to properly support the patient and maintain the patient's support relatively moisture and odor free.

2. Description of the Prior Art

Attempts have been made to remedy such conditions and to remove from the patient's support accumulations of urine. Exemplary of such prior art bed pads are those disclosed in U.S. Pat. Nos. 3,670,345; 3,989,867; and 3,757,356. Such exemplary prior art pads lack the important function of minimizing the generation and release of offensive odors.

SUMMARY OF THE INVENTION

Accordingly, it is an object of this invention to provide a patient underpad characterized by its ability to provide cushioning for a patient to readily absorb relatively large volumes of liquid in a manner such that the liquid absorbed does not thereafter irritate the patient and to reduce to a minimum generation and release of odors.

The present invention may be generally defined as a disposable patient underpad characterized by:

a first liquid impervious bottom layer;

a second liquid absorbing layer disposed on said bottom layer;

a third layer disposed on said liquid absorbing second layer, said third layer composed of a liquid impervious sheet having a plurality of spaced openings extending from face to face thereof, said opening being on the order of from about 1 to about 3 mm in cross dimension and spaced not closer than about 1 cm apart; and a fourth hydrophobic closed cell expanded foam body cushioning layer secured to said third layer, said fourth layer having a plurality of openings extending from face to face thereof said openings comprising at least about ¼ the total surface area of said fourth layer.

BRIEF DESCRIPTION OF THE DRAWING

FIG. 1 is a top plane view of a portion of a patient underpad constructed in accordance with the teachings of the present invention;

FIG. 2 is a section on line 2—2 of FIG. 1; and

FIG. 3 is an exploded fragmentary perspective view of a pad constructed in accordance with the teachings of this invention.

DESCRIPTION OF PREFERRED EMBODIMENTS

Referring to the drawing, 10 generally designates a disposable absorptive patient underpad. The pad 10 is composed of four laminated layers generally designated 12, 14, 16, and 18 each of which will be described in detail hereinafter.

The lowest or bottom layer 12 is composed of a thin liquid impervious preferably hydrophobic plastic sheet. The sheet 12 may be formed from polyethylene or polypropylene or similar relatively high strength liquid impervious materials. While polyethylene or polypropylene sheets are probably preferable materials, paper coated with a moisture impervious layer could be substituted for the plastic sheets.

The second layer 14 is the moisture absorbing layer and is formed of a hydrophilic material such as crepe cellulose material having good water absorption properties. In a form of the invention, the layer 14 may be composed of a plurality of thin layers of cellulosic material and to improve the hydrophilic and water and liquid absorbing properties thereof the layer 14 may be coated and/or impregnated with a conventional wetting agent.

It has been found that the layer or layers of liquid absorbing material 14 having a thickness of, for example, 3–5 mm normally provides sufficient liquid holding properties to carry out the intended function of such layer.

The next or third layer 16 comprises a hydrophobic liquid impervious sheet which may be the same as the bottom sheet 12 or different therefrom. The sheet 16 is provided with a plurality of perforations 20 which will permit the flow and wicking of liquids into the hydrophilic moisture absorbing layer 14. It has been found that openings in the order of from about 1 to about 3 mm is cross dimension and spaced not closer than about 1 cm apart will provide sufficient liquid drainage into the moisture absorbing layer 14 and at the same time reduce to a minimum the generation and release of odors from the moisture absorbing layer 14. By reducing the exposed upper surface area of the moisture absorbing sheet by the perforated hydrophobic third layer 16 odor formation in the body fluids absorbed in the layer 14 has been found to be retarded and at the same time the reduction in the exposed surface area assist in retaining any odors present or generated in the fluids contained in the moisture absorbing layer within such layer.

The fourth and top layer 18 of the improved pad is formed of a closed cell foam plastic material and preferably the foam closed cell plastic material is of a hydrophobic nature to thereby reduce to a minimum liquid retention on any of its surfaces. Any of the commercial closed cell plastic materials may be used for the layer 18, however, it has been found that the layers should have a relatively low density and be dimensionally stable to thereby provide cushioning for the patient while supporting the patient in spaced relation from the underlayer 16 and the moisture absorption layer 14. Closed cell blown polystyrene or polyurethane have been found to have satisfactory properties.

Further, a layer 18 having a thickness of about 1½ cm will generally provide sufficient cushioning and support to carry out the objects of the present invention. In order to permit liquids to flow from the top surface of layer 18 to the moisture absorbing layer 14, the closed cell hydrophobic foam plastic material 18 is formed with or thereafter provided with a plurality of relatively large openings 22. Openings in the order of 1½ cm and spaced ½ to 1 cm apart has been found to be entirely satisfactory. In addition to the major function of the openings 22, that is, to provide openings for the flow of body fluids from the patient to the absorption pad 14, the openings reduce the weight of the finished product and reduces the cost of the product by reducing the amount of plastic composition required in the upper layer 18.

Where desired, the top surface of the layer 18 may be covered with a thin layer of medical grade silicone to act as an anti-alergenic agent and to reduce possible irritation of the patient's skin.

In the illustrated form of the invention, it will be noted that the patient underpad has no edge seal. It has been found that, if the liquid absorbing layer 14 is of a highly hydrophilic nature, edge sealing is not necessary; however, if desired, the bottom layer 12 may have dimensions larger than the dimensions of the layers 14, 16 and 18 and brought upwardly to provide an edge seal as disclosed, for example, in U.S. Pat. Nos. 3,670,345 or 3,757,356.

It should also be noted that all or at least a majority of the openings 22 should coincide with the small openings 20 in the hydrophobic layer 16 to insure liquid drainage into the hydrophilic absorption layer 14. In the illustrated form of the invention, it will be noted that for each opening 20 there is one large opening 22 with the opening 20 centrally spaced in its cooperating opening 22. However, such uniformity of spacing is not a requirement of the moisture absorbing patient underpad 20 of the invention.

All of the layers 12, 14, 16 and 18 are laminated one to the other to provide a coherent unit. Lamination may be carried out by heat sealing where the layers are of a heat sealable material and/or by the use of suitable liquid adhesives, all as well known in the art.

Underpads constructed in accordance with the teachings of the present invention may be dispensed individually wrapped in a sterile condition in paper envelopes or in unsterile rolls of the material so that attendants may cut from the rolls pads of the desired size.

From the foregoing description of preferred and other embodiments of the present invention, it will be seen that, while specific terms have been employed in the description, they are used in a generic and descriptive sense only and not for purposes of limitation.

I claim:

1. A disposable patient underpad characterized by:
   a first liquid impervious bottom layer;
   a second coextensive liquid absorbing layer disposed on said bottom layer;
   a third coextensive layer disposed on said liquid absorbing second layer, said third layer composed of a liquid impervious sheet having a plurality of spaced openings extending from face to face thereof; said spaced openings in said third layer being of the order of from about 1 to about 3 mm in cross dimensions and spaced not closer than about 1 cm apart to provide liquid drainage into said second layer and to retard generation of odors in fluids contained in said second layer; and a fourth coextensive hydrophobic closed cell expanded foam body cushioning layer secured to said third layer, said fourth layer having a plurality of openings extending from face to face thereof, wherein the openings in said fourth layer are on the order of from about 1 to about 1½ cm in cross dimensions and spaced not closer than about 1 cm and said openings in the fourth layer comprising at least about ¼th the total surface area of said fourth layer and said openings in the fourth layer being vertically aligned with the openings in the third layer, said first, second, third and fourth layers being joined into an integral underpad.

* * * * *